(12) United States Patent
Kurihara et al.

(10) Patent No.: US 8,329,935 B2
(45) Date of Patent: Dec. 11, 2012

(54) PROCESS FOR PRODUCING PHOSPHORUS-CONTAINING DEHYDROAMINO ACID

(75) Inventors: Kenichi Kurihara, Kanagawa (JP); Nobuto Minowa, Kanagawa (JP); Nozomu Nakanishi, Kanagawa (JP); Masaaki Mitomi, Kanagawa (JP)

(73) Assignee: Meji Seika Kaisha Ltd., Tokyo (JP)

( * ) Notice: Subject to any disclaimer, the term of this patent is extended or adjusted under 35 U.S.C. 154(b) by 49 days.

(21) Appl. No.: 12/529,953

(22) PCT Filed: Mar. 19, 2008

(86) PCT No.: PCT/JP2008/055032
§ 371 (c)(1),
(2), (4) Date: Sep. 4, 2009

(87) PCT Pub. No.: WO2008/114808
PCT Pub. Date: Sep. 25, 2008

(65) Prior Publication Data
US 2011/0009662 A1    Jan. 13, 2011

(30) Foreign Application Priority Data
Mar. 19, 2007 (JP) .................. 2007-069958

(51) Int. Cl.
*C07F 9/28* (2006.01)
(52) U.S. Cl. ................................... 558/142
(58) Field of Classification Search .......... None
See application file for complete search history.

(56) References Cited

U.S. PATENT DOCUMENTS

| 4,922,006 A | 5/1990 | Zeiss |
| 2008/0146837 A1 | 6/2008 | Minowa et al. |
| 2009/0270647 A1 | 10/2009 | Minowa et al. |

FOREIGN PATENT DOCUMENTS

| JP | 62-226993 | 10/1987 |
| WO | 2006/104120 | 10/2006 |

OTHER PUBLICATIONS

Zeiss, H.-J. "Enantioselective Synthesis of Both Enantiomers of Phosphinothricin via Asymmetric Hydrogenation of α-Acylamido Acrylates" *J. Org. Chem.*, vol. 56, pp. 1783-1788, 1991.
Schmidt et al., "Diastereoselective Formation of (Z)-Didehydroamino Acid Esters" *Synthesis*, pp. 487-490, 1992.
Zu. Obshch. Khim. vol. 46, pp. 243-246, 1977.
Kober et al., "Untersuchungen zur Reaktion von Acylaminobrommalonestern und Acylaminobromessigestern mit Trialkylphosphiten—eine einfache Synthese von 2-Amino-2-(diethoxyphosphoryl)essig-saeure-ethylester" *Liebigs Ann. Chem.*, pp. 599-607, 1983.
International Search Report for PCT/JP2008/055032, mailed Apr. 15, 2008.
International Preliminary Report on Patentability for PCT/JP2008/055032, issued Sep. 22, 2009.
U.S. Appl. No. 12/530,022 to Minowa et al., entitled "Method for Producing Phosphorus-Containing Alpha-Keto Acid," which application is the National Stage of PCT/JP2008/055206, filed Mar. 21, 2008.
Organic Reactions, vol. 25, John Baldwin et al., Editors, pp. 73-74, 102, 146, and 249 (1977).

*Primary Examiner* — Paul A Zucker
(74) *Attorney, Agent, or Firm* — Greenblum & Bernstein, P.L.C.

(57) ABSTRACT

A process for efficiently producing through a small number of steps an N-substituted 2-amino-4-(substituted-oxymethylphosphinyl)-2-butenoic ester which is an intermediate for herbicide L-AMPB. The process comprises reacting a compound represented by the following formula (1): (where $R^1$ represents $C_{1-4}$ alkyl group) with a compound represented by the following formula (2): (wherein $R^2$, $R^{2'}$, and $R^3$ each represents $C_{1-4}$ alkyl and $R^4$ represents benzyloxycarbonyl) in the presence of a base.

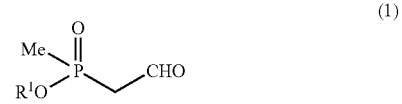

(1)

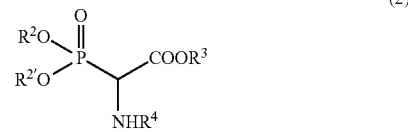

(2)

5 Claims, No Drawings

PROCESS FOR PRODUCING PHOSPHORUS-CONTAINING DEHYDROAMINO ACID

RELATED APPLICATION

This application claims the priority of Japanese Patent Application No. 2007-69958, filed Mar. 19, 2007, and the entire disclosure of the Japanese Application is incorporated herein by reference thereto.

TECHICAL FIELD

This invention relates to a process for producing N-substituted-2-amino-4-(substituted-oxymethylphosphinyl)-2-butenoic acid ester which is an intermediate of L-2-amino-4-(hydroxymethylphosphinyl)-butanoic acid (abbreviated as "L-AMPB" hereinafter) that is useful as an herbicide.

BACKGROUND ART

It has been hitherto known that N-substituted-2-amino-4-(substituted-oxymethylphosphinyl)-2-butenoic acid ester is a synthesis-intermediate of L-AMPB having herbicidal activity (Japanese Patent Kokai Publication No. S62-226993A (1987) (Patent Document 1) and J. Org. Chem., 56, 1991, 1783-1788(Non Patent Document 1)).

Up to date, a process for synthesizing by condensing 2-oxo-4-(hydroxymethylphosphinyl)-butenoic acid with acetamide and a process for synthesizing by condensing a derivative of phosphinylacetaldehyde with isocyanoacetate have been reported as a processes for producing N-substituted-2-amino-4-(substituted-oxymethylphosphinyl)-2-butenoic acid ester. (Patent Document 1).

The process for synthesizing dehydroamino acid by a reaction of the Horner-Emmons type with a derivative of phosphorylglycine and aldehyde has been known (Synthesis, 1992, 487(Non Patent Document 2)).

Patent Document 1: Japanese Patent Kokai Publication No. S62-226993A (1987)
Non Patent Document 1: J. Org. Chem., 56, 1991, 1783-1788
Non Patent Document 2: Synthesis, 1992, 487

SUMMARY

The following analysis is provided by the present invention. The entire disclosures in each of said Patent Document 1, and Non Patent Documents 1 and 2 are incorporated and described herein by reference thereto.

However, the processes of Patent Document 1 and Non Patent Document 1 have problems such that the steps are numerous, the yield is low, and the reagents are expensive, therefore, establishment of a more efficient producing process is desired.

In addition, in Patent Document 2, any example in which application was made in the reaction with aldehyde compounds having polar substituted group such as phosphorus, has not been known.

It is an object of the present invention to provide a process for producing N-substituted-2-amino-4-(substituted-oxymethylphosphinyl)-2-butenoic acid ester which is a production intermediate of L-AMPB that is useful as an herbicide in short steps and efficiently.

The present inventors examined the reaction of a derivative of phosphorylglycine and a derivative of phosphorus-including aldehyde in detail, and as a result they found that N-substituted-2-amino-4-(substituted-oxymethylphosphinyl)-2-butenoic acid ester is obtained in high yield by a reaction using a base, and completed the present invention.

That is to say, in a first aspect, the present invention provides a process for producing a compound represented by the following formula (3):

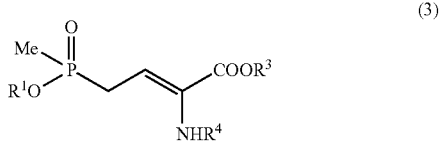

[where $R^1$ represents $C_{1-4}$ alkyl group, aryl group, substituted aryl group, aryl methyl group or substituted aryl methyl group,
$R^3$ represents $C_{1-4}$ alkyl group, aryl methyl group or substituted aryl methyl group, and
$R^4$ represents $C_{2-4}$ alkanoyl group, benzoyl group, benzyl group, $C_{1-4}$ alkyloxy carbonyl group or benzyloxy carbonyl group] comprising a step of reacting a compound represented by the following formula (1):

[where $R^1$ represents the same meaning as the definition described above] with a compound represented by the following formula (2):

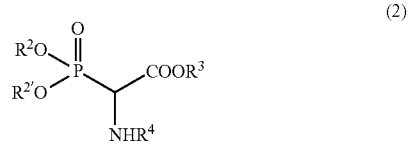

[where $R^2$ and $R^{2'}$ represent identically or differently $C_{1-4}$ alkyl group, aryl group, substituted aryl group, aryl methyl group or substituted aryl methyl group, and $R^3$ and $R^4$ represent the same meaning as the definitions described above] in the presence of base.

N-substituted-2-substituted amino-4-(substituted-oxymethylphosphinyl)-2-butenoic acid ester which is a production intermediate of an herbicide L-AMPB can be produced by the inventive process. As the process which can synthesis inexpensively, in short steps and efficiently, the inventive process is superior to the conventional processes. Therefore, the present invention is industrially significantly useful, especially in the field of agents for which the herbicidal effect is required.

PREFERRED MODE(S)

The groups represented by $R^1$, $R^2$, $R^{2'}$, $R^3$ and $R^4$ in the compounds represented by formula (1) to formula (3) are explained.

$C_{1-4}$ alkyl group(s) represented by $R^1$, $R^2$, $R^{2'}$ and $R^3$ refers to straight or branched alkyl group(s) having 1-4 carbon atom(s); more specifically, are exemplified by methyl group, ethyl group, n-propyl group, isopropyl group, n-butyl group, 2-butyl group, isobutyl group, t-butyl group or the like.

The group(s) represented by $R^1$, $R^2$, $R^{2'}$ and $R^3$ or aryl group existing on the group(s) is(are) exemplified by phenyl group, naphthyl group or the like.

The aryl methyl group(s) represented by $R^1$, $R^2$, $R^{2'}$ and $R^3$ refers to a methyl group substituted by 1-3 of aryl group(s); more specifically, is(are) exemplified by benzyl group, diphenyl methyl group, fluorenyl group, triphenyl methyl group or the like.

The substituted aryl group(s) represented by $R^1$, $R^2$ and $R^{2'}$ denotes that 1 or more hydrogen atoms, preferably, 1 to 3 hydrogen atom(s) on the benzene ring is(are) substituted, and the specific substitutes are exemplified by straight or branched $C_{1-4}$ alkyl group such as methyl group, ethyl group, n-propyl group, isopropyl group, n-butyl group, 2-butyl group, isobutyl group and t-butyl group; halogen atom(s) such as fluorine atom, chlorine atom and bromine atom, and $C_{1-4}$ alkoxy group such as methoxy group.

The substituted aryl methyl group(s) represented by $R^1$, $R^2$, $R^{2'}$ and $R^3$ denotes to that 1 or more hydrogen atom(s), preferably, 1 to 3 hydrogen atom(s) on the benzene ring is(are) substituted, and the specific substitutes are exemplified by straight or branched $C_{1-4}$ alkyl group such as methyl group, ethyl group, n-propyl group, isopropyl group, n-butyl group, 2-butyl group, isobutyl group and t-butyl group; halogen atom(s) such as fluorine atom, chlorine atom and bromine atom, and $C_{1-4}$ alkoxy group such as methoxy group.

The $C_{2-4}$ alcanoyl group represented by $R^4$ refers to straight or branched alcanoyl group having 2 to 4 carbons; more specifically, it is exemplified by acetyl group, n-propanoyl group, n-butanoyl group, isobutanoyl group or the like.

The $C_{1-4}$ alkyloxycarbonyl group represented by $R^4$ refers to straight or branched alkyloxycarbonyl group; more specifically, it is exemplified by methoxycarbonyl group, ethoxycarbonyl group, n-propyloxycarbonyl group, isopropyloxycarbonyl group, n-butyloxycarbonyl group, 2-butyloxycarbonyl group, isobutyloxycarbonyl group, t-butyloxycarbonyl group or the like.

In the compounds represented by formula (1) and formula (3), $R^1$ is, preferably, $C_{1-4}$ alkyl group, more preferably, methyl group and ethyl group.

As concrete examples of the compound represented by formula (1), the following is exemplified:
2-(methoxy(methyl)phosphinyl)-acetaldehyde,
2-(ethoxy(methyl)phosphinyl)-acetaldehyde,
2-(n-propyloxy(methyl)phosphinyl)-acetaldehyde;
2-(n-butyloxy(methyl)phosphinyl)-acetaldehyde,
2-(phenoxy(methyl)phosphinyl)-acetaldehyde,
2-(p-tolyloxy(methyl)phosphinyl)-acetaldehyde,
2-(benzyloxy(methyl)phosphinyl)-acetaldehyde, and
2-(p-chlorobenzyloxy(methyl)phosphinyl)-acetaldehyde;
preferably, 2-(ethoxy(methyl)phosphinyl)-acetaldehyde.

The compound of formula (1) can be synthesized by the process described in Zu. Obshch. Khim., 46, 1977, 243. (The disclosure of this literature is incorporated herein by reference thereto.)

In the compound of formula (2), $R^2$ and $R^{2'}$ are preferably, identically or differently $C_{1-4}$ alkyl group or aryl group, more preferably, for both $C_{1-4}$ alkyl group.

In the compounds of formula (2) and formula (3), $R^3$ is, preferably, $C_{1-4}$ alkyl group, and $R^4$ is, preferably, $C_{2-4}$ alcanoyl group, $C_{1-4}$ alkyloxycarbonyl group or benzyloxycarbonyl group, more preferably, benzyloxycarbonyl group.

Therefore, in formula (2), a compound(s), wherein $R^2$ and $R^{2'}$ are $C_{1-4}$ alkyl group(s), $R^3$ is $C_{1-4}$ alkyl group and $R^4$ is $C_{2-4}$ alcanoyl group, $C_{1-4}$ alkyloxycarbonyl group or benzyloxycarbonyl group, is more preferable.

In formula (3), a compound(s), wherein $R^1$ is $C_{1-4}$ alkyl group, $R^3$ is $C_{1-4}$ alkyl group and $R^4$ is $C_{2-4}$ alcanoyl group, $C_{1-4}$ alkyloxycarbonyl group or benzyloxycarbonyl group, is more preferable.

In addition, as a preferred embodiment of the present invention, the process, wherein $R^1$ in formula (1) is $C_{1-4}$ alkyl group, $R^2$, $R^{2'}$ and $R^3$ in formula (2) are $C_{1-4}$ alkyl groups, $R^4$ is benzyloxycarbonyl group; and $R^1$, $R^3$ and $R^4$ on formula (3) are a group(s) corresponding to these, is exemplified.

As concrete examples of the compound represented by formula (2), the following compounds are exemplified. In the concrete examples, Ph represents phenyl group, Me represents methyl group and Et represents ethyl group.

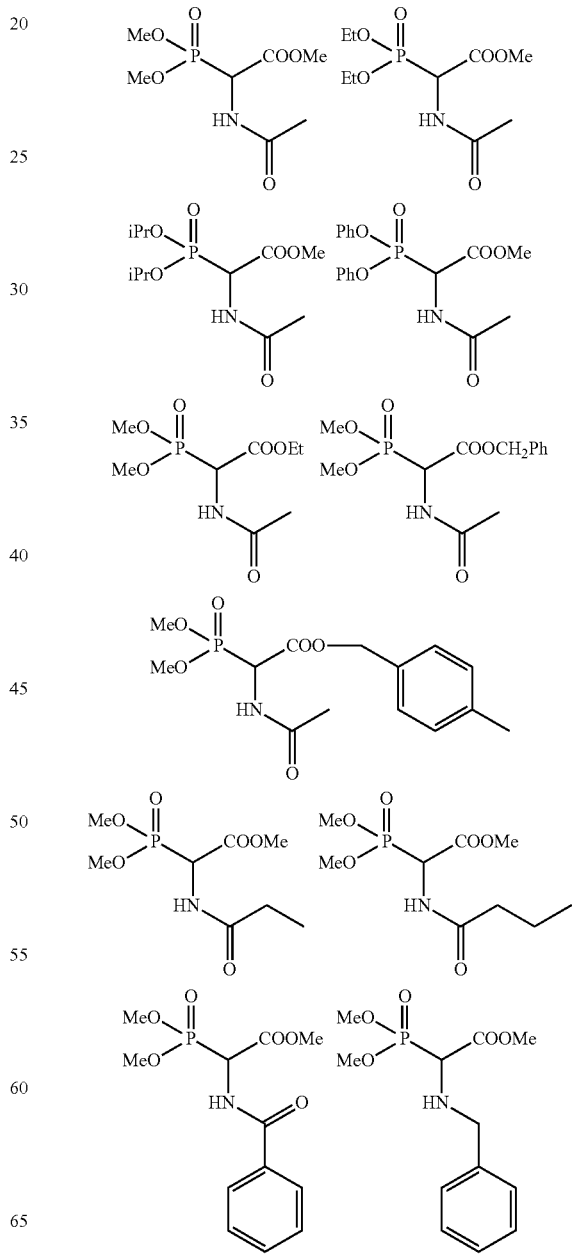

-continued

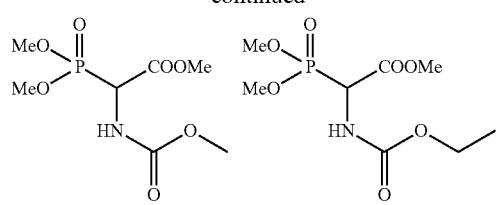
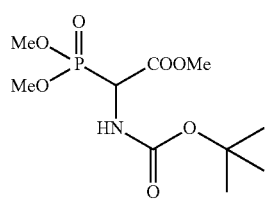
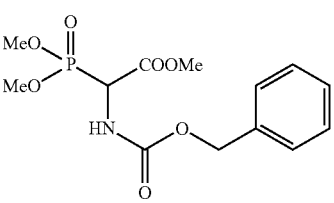

Preferred compounds are the following.

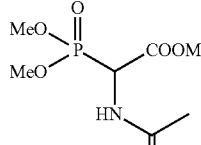
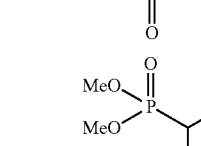
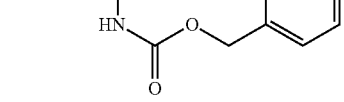

The compound of formula (2) can be synthesized by a process described in Liebigs Ann. Chem., 1983, 599. (The disclosure of this literature is incorporated herein by reference thereto.)

As concrete examples of the compound of formula (3), following compounds are exemplified. In the concrete examples, Ph represents phenyl group, Me represents methyl group and Et represents ethyl group.

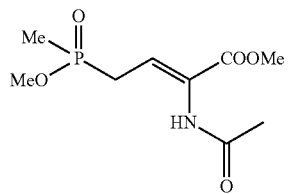

-continued

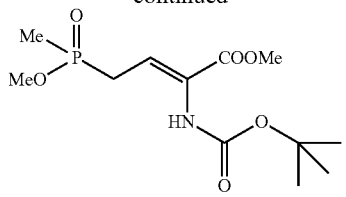
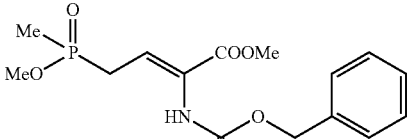
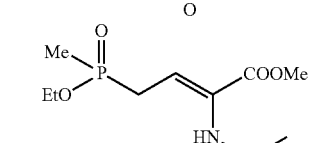
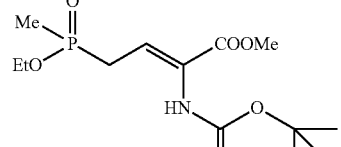
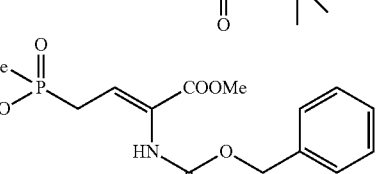
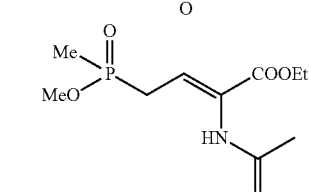
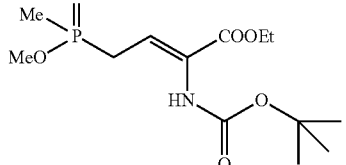
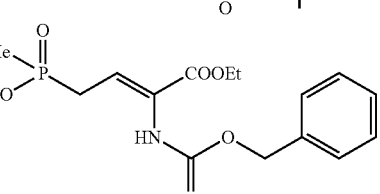
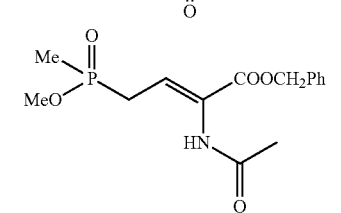

-continued

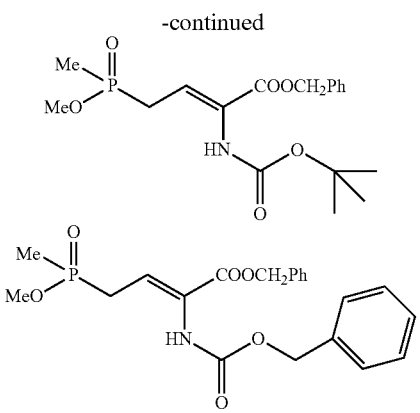

Preferred compounds are the following.

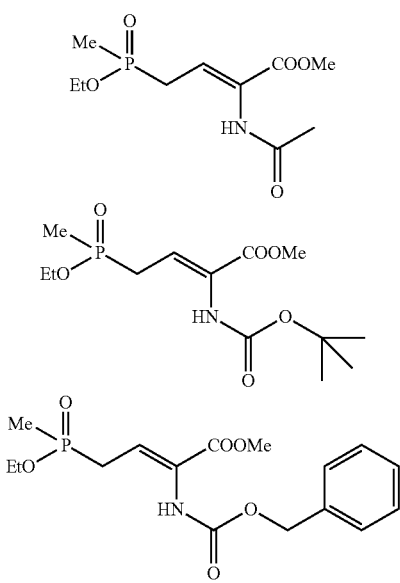

As a solvent to be used in the process for producing the compound represented by formula (3) from the compound of formula (1) and the compound of formula (2), the following is exemplified: halogenated hydrocarbon solvent such as methylene chloride and chloroform; aromatic hydrocarbon solvent such as benzene and toluene; ether solvent such as tetrahydrofuran, dimethoxyethane and dioxane; aprotic polar organic solvent such as N—N-dimethylformamide and dimethyl sulfoxide; or alkanol solvent having 1 to 4 carbon atom(s) such as methanol, preferably, methylene chloride, chloroform or tetrahydrofuran.

The base to be used is exemplified by sodium hydride, potassium hydride, n-butyllithium, lithium diisopropylamide, dimsyl sodium, sodium methoxide, sodium ethoxide, potassium t-butoxide and tetramethylguanidine, preferably, potassium t-butoxide or tetramethylguanidine.

Bases are used in an amount of 1 to 1.4 equivalents based on the amount of the compound(s) represented by formula (1).

An amount used of the compound represented by formula (2) is, preferably, within an amount of 1 to 1.4 equivalents based on the amount of compound(s) represented by formula (1), and the compound(s) represented by formula (2), and the base(s) is used in the same amount of equivalents.

A reaction temperature at which the base and the compound of formula (1) are admixed into the solvent including the compound(s) of formula (2) is within a temperature range of −78° C. to 0° C., preferably within a range of −78° C. to −30° C. The reaction time is usually within a time range of 10 minutes to 2 hours, preferably, within a range of 30 minutes to 1 hour. After that, the reaction temperature is raised to a temperature range of 0° C. to 50° C., preferably, to a range of 15° C. to 30° C. The reaction time after rising temperature is within a time range of 2 hours to 8 hours, preferably, within a range of 3 hours to 5 hours.

After completion of the reaction, the compound represented by formula (3) can be isolated by vacuum concentrating the reaction solution and purification using silica gel chromatography etc.

N-substituted-2-amino-4-(substituted-oxymethylphosphinyl)-2-butenoic acid ester obtained by the present invention can be converted to L-AMPB by the processes described in Japanese Patent Kokai Publication No. S62-226993A (1987), WO2006/104120A and WO2008/029754A. (The disclosures of those literatures are incorporated herein by reference thereto.)

EXAMPLES

Hereinafter, the present invention is specifically explained by way of examples, but is not limited to these examples. N-(benzyloxycarbonyl)-alpha-phosphonoglycine trimethyl ester, which was commercially available from Aldrich, was used. 2-(ethoxy(methyl)phosphinyl)-acetaldehyde was synthesized according to the process described in Zu. Obshch. Khim., 46, 1977, 243.

Example 1

Production of methyl (Z)-N-(benzyloxycarbonyl)-2-amino-4-(ethoxy(methyl)phosphinyl)-2-butenoate After 214 mg of N-(benzyloxycarbonyl)-alpha-phosphonoglycine trimethyl ester was dissolved in 5 ml of methylene chloride, 74 mg of potassium t-butoxide was added, followed by stirring at −78° C. for 30 minutes. 76.5 mg of 2-(ethoxy (methyl)phosphinyl)-acetaldehyde in methylene chloride solution (1 ml) was gradually added dropwise into this reaction solution, which was stirred for 1 hour. After the reaction temperature was gradually raised up to room temperature, further the reaction solution was stirred for 3 hours. Consuming of ingredients was confirmed by using TLC, and the solvent was removed off under reduced pressure. The residual was purified by silica gel column chromatography (chloroform-methanol (100:1-50:1)), 168 mg of an objective compound was obtained (93% yield).

Physicochemical Properties of the Present Compound $^1$H NMR (CDCl$_3$) δ: 1.24(t, 3H, J=7.5 Hz), 1.41(d, 3H, J=15 Hz), 2.68(q, 1H, J=7.5 Hz), 2.73(q, 1H, J=7.5 Hz), 3.68(s, 3H), 3.99(m, 2H), 5.16(s, 2H), 6.37(dd, 1H, J=7.5 Hz, 15 Hz), 7.28(m, 5H).

FABMASS: m/z 356 [M+H]$^+$

The above description is based on the example, but the present invention is not limited to above described example. Within the framework of the entire disclosure of the present invention (including claims), and on the basis of the basic technical teachings thereof, embodiments and example can be altered and modified. Within the framework of claims, the various disclosed factors can be variously combined, substituted and selected. The patent applications and the literatures referenced in this application are incorporated in this application by reference thereto.

The invention claimed is:
1. A process for producing a compound represented by the following formula (3):

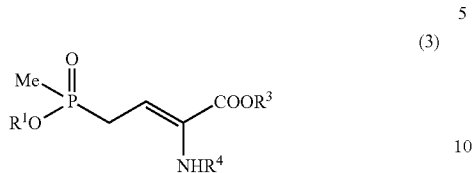

[where $R^1$ represents a $C_{1-4}$ alkyl group, an aryl group, a substituted aryl group, an aryl methyl group or a substituted aryl methyl group,
$R^3$ represents a $C_{1-4}$ alkyl group, an aryl methyl group or a substituted aryl methyl group, and
$R^4$ represents a $C_{2-4}$ alkanoyl group, a benzoyl group, a benzyl group, a $C_{1-4}$ alkyloxy carbonyl group or a benzyloxy carbonyl group]
comprising: reacting a compound represented by the following formula (1):

[where $R^1$ represents the same meaning as the definitions described above]
with a compound represented by the following formula (2):

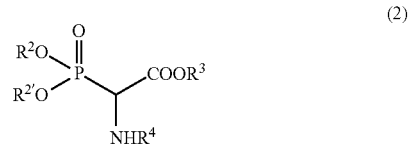

[where $R^2$ and $R^{2'}$ represent identically or differently a $C_{1-4}$ alkyl group, an aryl group, a substituted aryl group, an aryl methyl group, or a substituted aryl methyl group, and $R^3$ and $R^4$ represent the same meaning as the definition described above]
in the presence of a base.

2. The process as defined in claim 1, wherein the base is any one selected from a class of sodium hydride, potassium hydride, n-butyllithium, lithium diisopropylamide, dimsylsodium, sodium methoxide, sodium ethoxide, potassium t-butoxide and tetramethylguanidine.

3. The process as defined in claim 1, wherein $R^1$, $R^2$, $R^{2'}$ and $R^3$ are a $C_{1-4}$ alkyl group and $R^4$ is a benzyloxycarbonyl group.

4. The process as defined in claim 2, wherein $R^1$, $R^2$, $R^{2'}$ and $R^3$ are a $C_{1-4}$ alkyl group and $R^4$ is a benzyloxycarbonyl group.

5. The process as defined in claim 1, wherein the base is potassium t-butoxide.

* * * * *

UNITED STATES PATENT AND TRADEMARK OFFICE
CERTIFICATE OF CORRECTION

PATENT NO. : 8,329,935 B2
APPLICATION NO. : 12/529953
DATED : December 11, 2012
INVENTOR(S) : K. Kurihara et al.

It is certified that error appears in the above-identified patent and that said Letters Patent is hereby corrected as shown below:

Title Page, Item (73) Assignee: "Meji Seika Kaisha Ltd." should be
-- MEIJI SEIKA KAISHA LTD. --.

Title Page, Item (56), References Cited, Other Publications, column 2, line 12,
"pp. 599-607" should be -- pp. 599-609 --.

Signed and Sealed this
Sixteenth Day of July, 2013

Teresa Stanek Rea
*Acting Director of the United States Patent and Trademark Office*